(12) United States Patent
Nettelroth et al.

(10) Patent No.: US 10,646,112 B2
(45) Date of Patent: May 12, 2020

(54) ADAPTIVE LARYNGOSCOPE AND ADAPTIVE BLADE FOR A LARYNGOSCOPE

(71) Applicant: Karl Storz SE & Co. KG, Tuttlingen (DE)

(72) Inventors: Vincent Nettelroth, Mühlhausen-Ehingen (DE); Roland Hagen, Spaichingen (DE); Christopher Deppisch, Engen (DE); Marcus Brechtold, Tuttlingen (DE); Ulrich Merz, Tuttlingen (DE); Eugenia Fuhr, Tuttlingen (DE); Petra Kupferschmid, Tuttlingen (DE); Andreas Efinger, Tuttlingen (DE); Ralf Staud, Tuttlingen (DE)

(73) Assignee: Karl Storz SE & Co. KG, Tuttlingen (DE)

( * ) Notice: Subject to any disclaimer, the term of this patent is extended or adjusted under 35 U.S.C. 154(b) by 0 days.

(21) Appl. No.: 15/642,805

(22) Filed: Jul. 6, 2017

(65) Prior Publication Data
US 2018/0020906 A1 Jan. 25, 2018

(30) Foreign Application Priority Data
Jul. 6, 2016 (DE) ........................ 10 2016 112 385

(51) Int. Cl.
| | |
|---|---|
| *A61B 1/00* | (2006.01) |
| *A61B 1/267* | (2006.01) |
| *A61B 1/005* | (2006.01) |
| *A61B 1/06* | (2006.01) |

(52) U.S. Cl.
CPC ............ *A61B 1/267* (2013.01); *A61B 1/0055* (2013.01); *A61B 1/00105* (2013.01); *A61B 1/0676* (2013.01); *A61B 1/0008* (2013.01)

(58) Field of Classification Search
CPC ....... A61B 1/267; A61B 1/2676; A61B 1/273; A61B 1/2733; A61B 1/2736
USPC .................................................. 600/185–200
See application file for complete search history.

(56) References Cited

U.S. PATENT DOCUMENTS

| | | | | |
|---|---|---|---|---|
| 5,938,591 | A * | 8/1999 | Minson ................. | A61B 1/267 600/191 |
| 2005/0054903 | A1* | 3/2005 | Cantrell ............. | A61B 1/00094 600/196 |

FOREIGN PATENT DOCUMENTS

| | | | | |
|---|---|---|---|---|
| CN | 106236001 A | | 12/2016 | |
| WO | WO 2016/074894 | * | 5/2016 | ............. A61B 1/267 |
| WO | WO-2016074894 A2 | * | 5/2016 | ........... A61B 1/0056 |

* cited by examiner

*Primary Examiner* — Julianna N Harvey
*Assistant Examiner* — Christina Negrellirodriguez
(74) *Attorney, Agent, or Firm* — Whitmyer IP Group LLC (57) ABSTRACT

An adaptive blade for a laryngoscope includes a proximal end, which is mechanically connectable or connected to a handle in order to form an adaptive laryngoscope, a first flexible bar, which extends from the proximal end of the adaptive blade to the distal end thereof, and a second flexible bar, which extends from the proximal end of the adaptive blade to the distal end thereof. At the distal end of the adaptive blade, the flexible bars are connected to each other mechanically rigidly or in an articulated manner. In the proximal direction from the distal end of the adaptive blade, the flexible bars are mechanically connected to each other in such a way that they are movable relative to each other substantially in their longitudinal directions.

19 Claims, 3 Drawing Sheets

Fig. 8 ary bars. The guide channel can also be formed in one piece with the first flexible bar or with the second flexible bar or with one or more of several second flexible bars.

ADAPTIVE LARYNGOSCOPE AND ADAPTIVE BLADE FOR A LARYNGOSCOPE

TECHNICAL FIELD

The present invention relates to an adaptive laryngoscope, in particular an adaptive intubation laryngoscope, or an adaptive laryngoscope for surgery of the larynx or for other purposes in otorhinolaryngology, and also to an adaptive blade for such a laryngoscope.

BACKGROUND

To perform endotracheal intubation in anesthesia, emergency medicine and intensive care and to perform surgery of the larynx, an unobstructed access to the larynx, the vocal cords and, ultimately, the trachea is needed for the intubation or the surgical procedures. In these cases, a laryngoscope is used to push the tongue forward or in the rostral direction. A laryngoscope generally comprises a blade of greater or lesser curvature, at the proximal end of which blade a handle is arranged approximately at a right angle.

To facilitate adaptation to the anatomy of the patient, the blade is generally exchangeable. An intubation kit includes a large number of blades of different length and different curvature. Moreover, different designs of blade are available for different uses and/or to meet different preferences of the medical personnel, for example blades after Macintosh, Miller, Dörges and McCoy, the latter with a movable distal end.

A laryngoscope with a deformable distal end is also described in WO 97/30626. The blade 4 of the laryngoscope has several slits 40 in a central portion 14. The slits 40 divide the central portion 14 into segments 42, which are connected to each other only by narrow webs that act as flexure bearings.

EP 1 040 999 A2 describes a component for taking up forces, in which struts 11, 11a connect opposite regions of an outer skin 12, 12a to each other.

EP 2 241 403 A1 describes a manipulator tool with two flexible cheeks 8, 10. At the distal end 6 of the manipulator tool 1, the cheeks 8, 10 are connected to each other directly and also by several hinge elements 20.

DE 10 2007 026 721 A1 describes a medical gripping tool for holding body parts. The medical gripping tool 1 comprises several branches 1, each with two opposite cheeks between which connecting elements extend.

In WO 2016/074894 A2, an intubation laryngoscope comprising a handle 1 and a curved intubation blade 2 is described. The intubation blade 2 comprises a flexible blade body having two blade half-shells 2a, 2b and a blade tongue 6. The distal end of the blade tongue 6 is fixed to the blade tip 3. The blade half-shells 2a, 2b have guiding brackets rectangularly bent towards each other and forming a guide 11. Guiding slides 13 at the blade tongue 6 engage into the guide 11.

In US 2013/0310650 A1, a laryngoscope 1 with a blade 5 is described. A sheath 9, 80, 100 for the blade 5 can be attached to the laryngoscope 1.

It is an object of the present invention to make available an improved adaptive blade for a laryngoscope and to make available an improved adaptive laryngoscope.

SUMMARY

This object is achieved by the subject matter of the independent claims.

Developments are set forth in the dependent claims.

An adaptive blade for a laryngoscope comprises a proximal end, which is mechanically connectable or connected to a handle in order to form an adaptive laryngoscope, a first flexible bar, which extends from the proximal end of the adaptive blade to the distal end thereof, and a second flexible bar, which extends from the proximal end of the adaptive blade to the distal end thereof, wherein, at the distal end of the adaptive blade, the flexible bars are connected to each other mechanically rigidly or in an articulated manner, and wherein, in the proximal direction from the distal end of the adaptive blade, the flexible bars are mechanically connected to each other in such a way that they are movable relative to each other substantially in their longitudinal directions.

The adaptive blade is provided and designed in particular to form a laryngoscope which is usable for intubation or for microsurgery of the larynx or for other purposes in otorhinolaryngology. The proximal end of the adaptive blade can be mechanically connected to a handle in a permanent manner, in particular for the full expected lifetime of the laryngoscope, so as not to be separable without destruction. In particular, the adaptive blade can be formed completely or partially in one piece with the handle, for example as a simultaneously produced molding made of plastic, metal or another sufficiently elastic material. Alternatively, a coupling mechanism (for example in the form of a bayonet connection, a screw connection or a latch connection) can be provided at the proximal end of the adaptive blade for the purpose of coupling the latter to a handle in such a way as to be releasable therefrom without destruction, either once or repeatedly.

Particularly, under the forces that occur during the intended use, each of the two flexible bars is only slightly elastically or plastically deformable, if at all, in the longitudinal direction. The elastic or plastic deformability of the flexible bars in the longitudinal direction is in particular so low that a curvature of the adaptive blade, brought about by a relative displacement of proximal ends of the flexible bars or by external forces acting on the adaptive blade, is reduced by not more than 50% or by not more than 20% or by not more than 10% or by not more than 5% or by not more than 2% or by not more than 1% compared to bars that are ideally completely inelastic in the longitudinal direction.

The flexible bars are each elastically and/or plastically bendable to any appreciable extent in particular only in one direction, and they are each substantially flexurally stiff in a direction orthogonal thereto. A flexibility in a first direction or a first plane and a flexural stiffness in a second direction or second plane orthogonal thereto and a low deformability in the longitudinal direction can be achieved, for example, by a flat cross section of a bar, which has a substantially smaller extent in the first direction than in the second direction. The two flexible bars are each made in particular from a polymer, another plastic or a metal.

The first flexible bar is in particular provided and arranged to rest on a patient's tongue during the intended use. For this purpose, the first flexible bar is in particular broad and flat and has a smooth surface provided to rest on the tongue. Instead of a single second flexible bar, it is possible to provide two or more flexible second bars, in particular arranged parallel or substantially parallel to each other. A space between two second flexible bars can be used for the insertion of a tube, an endoscope and/or another medical instrument. For this purpose, a guide channel with an open or closed cross section can be provided. This guide channel can be rigidly connected to the first flexible bar or to the second flexible bar or to one or more of several second flexible bars, particularly formed in one piece therewith. Moreover, a light source, for example a light-emitting diode, or a fiber optic cable for transmission of illumination light, a camera or an image sensor with imaging optics or a flexible endoscope can be connectable or permanently connected to one of the flexible bars, in particular at or near the distal end thereof. A connection is permanent if it is designed to exist for a period of time covering several medical interventions or for the full expected lifetime of the laryngoscope.

An adaptive blade with features and properties described here can be adapted to the anatomy of a patient by medical personnel. Alternatively or in addition, during the intended use, an adaptive blade with features and properties described here can completely or partially adapt automatically, by elastic and/or plastic deformation, to a patient's anatomy, in particular to the curvature, shape and/or size of the tongue or of the pharynx of the patient. This adaptation to the patient's anatomy is facilitated in particular by the flexural elasticity of the two bars and by the mechanical connection of the two flexurally elastic bars, in such a way that the two flexurally elastic bars are movable relative to each other substantially in their longitudinal directions, but the distances between them are not substantially alterable. This facilitates a merely local retreat of the adaptive blade. For example, the adaptive blade can retreat at a convex region of the surface of a patient's tongue, while a distal region of the adaptive blade can however rest at a concave region of the surface of the tongue. The adaptive blade can thus apply a comparatively uniform pressure to the surface of the tongue, specifically both in concave regions and also in convex regions of the surface of the tongue.

An adaptive blade of this kind can thus be used for patients with different anatomical characteristics, and therefore the number of blades that have to be kept in stock can be significantly reduced. Moreover, time can be saved particularly in emergency medicine, since a blade does not first of all have to be selected and connected to the handle; instead, an adaptive blade already connected to a handle is adapted and/or adapts during its use to the anatomy of a patient.

An adaptive blade as described here further comprises in particular a strut which, in the proximal direction from the distal end of the adaptive blade, mechanically connects the first flexible bar and the second flexible bar to each other.

The ends of the strut are connected to the flexible bars in particular by flexure bearings or other hinges. Alternatively, the whole strut can be designed as a flexure bearing or be made elastic.

An adaptive blade as described here further comprises in particular a thin and flexible connecting component which is alternately connected to the first flexible bar and to the second flexible bar.

The thin and flexible connecting component is in particular flexurally slack. The thin and flexible connecting component comprises in particular a wire, a fiber, a filament, a thread or a thin cable. The thin and flexible connecting component can have, for example, polyester, HPPE (high-performance polyethylene, also known by the brand name Dyneema) or another polyethylene. The thin and flexible connecting component can extend over the entire adaptive blade or a part of the adaptive blade.

If the adaptive blade has several second flexible bars, one thin and flexible connecting part can be provided to connect all of the second flexible bars to the first flexible bar. Alternatively, several thin and flexible connecting parts can be provided, in which case, for example, each thin and flexible connecting component is provided to connect a second flexible bar to the first flexible bar.

The thin and flexible connecting component is in particular connected alternately to the first flexible bar and to the second flexible bar in such a way that it has a meandering configuration. Those portions of the thin and flexible connecting component that connect the flexible bars to each other are in particular parallel or substantially parallel to each other. This applies in particular to respectively adjacent portions of the thin and flexible connecting component.

The thin and flexible connecting component can transmit tensile forces between the flexible bars and can define a maximum distance between the flexible bars.

An adaptive blade as described here further comprises in particular eyelets or other guiding mechanisms at the flexible bars, wherein the thin and flexible connecting component is alternately guided through guiding mechanisms at the first flexible bar and through guiding mechanisms at the second flexible bar.

Each guiding mechanism has in particular an annular or tubular configuration. In particular, the eyelets or other annular guiding mechanisms at one flexible bar have constant or substantially constant distances from each other, or distances that only slowly vary along the flexible bar, and the thin and flexible connecting component is in each case guided alternately through two guiding mechanisms at the first flexible bar and through two guiding mechanisms at the second flexible bar. Alternatively, tubular guiding mechanisms are provided for example, in which case the distance between two adjacent guiding mechanisms corresponds substantially to the length of a guiding mechanism, wherein the thin and flexible connecting component is in each case guided alternately through a guiding mechanism at the first flexible bar and through a guiding mechanism at the second flexible bar.

In an adaptive blade as described here, the thin and flexible connecting component is mounted displaceably, in particular in each case in its longitudinal direction, in the eyelets or other guiding mechanisms.

In particular, the ends of the thin and flexible connecting component are firmly connected to the adaptive blade, for example to one or more ends of the flexible bars. A displaceability of the thin and flexible connecting component in the eyelets or other guiding mechanisms can facilitate substantial compensation of mechanical stresses and can thus support uniform deformation of the adaptive blade.

Alternatively, everywhere it is connected to the first flexible bar or to the second flexible bar, the thin and flexible connecting component can be connected thereto rigidly or at least non-displaceably in its longitudinal direction.

In an adaptive blade as described here, the thin and flexible connecting component in particular comprises a wire made of a pseudoelastic nickel-titanium alloy or of another pseudoelastic material, or a wire made of another material.

Unlike a thread or a string, a wire made of a pseudoelastic nickel-titanium alloy (for example known by the name Nitinol) or of another pseudoelastic material and/or elastic material (for example metal, polyester or another plastic) can have a closed and pore-free surface, which can make cleaning and sterilizing much easier.

An adaptive blade as described here further comprises in particular an arc-shaped portion at the second end of the second flexible bar.

The arc-shaped portion at the second end of the second flexible bar is in particular circular-arc-shaped or substantially circular-arc-shaped.

An adaptive blade as described here further comprises in particular spoke mechanisms, of which first ends are mechanically connected to the proximal end of the first flexible bar, and of which second ends are mechanically connected to the arc-shaped portion of the second flexible bar.

The first or radially inner ends of the spoke mechanisms are in particular each mechanically connected in an articulated manner to the proximal end of the first flexible bar, directly or indirectly. The second or radially outer ends of the spoke mechanisms are in particular each mechanically connected in an articulated manner to the arc-shaped portion. The articulated connections can be configured as flexure bearings or as hinges based on form-fit engagement. The spoke mechanisms can each be thin and flexible along their entire length, so as not to unnecessarily concentrate a deformation and material fatigue at one location.

The arc-shaped portion at the proximal end of the second flexible bar, guided through the described spoke mechanisms or in another way, is able to facilitate a deflection of forces and movements. In particular, longitudinal movements of the second flexible bar (and corresponding tensile or compressive forces in the second flexible bar) can be coupled through the arc-shaped portion with movements of an operating element, which is movable parallel to a handle connected to the blade, (and corresponding forces applied manually to the operating element).

An adaptive blade as described here further comprises in particular an elastic jacket for protecting the adaptive blade from contamination and other environmental influences.

The elastic jacket has in particular an elastic film, an elastic woven fabric, an elastic knit and/or an elastic non-woven or another elastic sheet-like, film-like or textile-like material. The elastic jacket can be permanently connected to the adaptive blade or can be provided for replacement after each use. A connection is permanent if it is designed to exist for a period of time covering several medical interventions or for the full expected lifetime of the laryngoscope.

An adaptive blade as described here further comprises in particular a form-fit connection of the two flexible bars proximally with respect to the distal end of the adaptive blade, which form-fit connection facilitates a movement of the two flexible bars relative to each other in a first predetermined direction and, by form-fit engagement, suppresses a movement of the two flexible bars relative to each other in a second predetermined direction, which is orthogonal to the first predetermined direction.

The adaptive blade can have several form-fit connections of the two flexible bars. The first predetermined direction is in particular parallel or substantially parallel to at least one of the two flexible bars or to the longitudinal direction thereof. The form-fit connection suppresses a movement of the two flexible bars relative to each other in a direction orthogonal thereto or in all directions orthogonal thereto, in particular except for inevitable play, or except for play that is unavoidable for production reasons.

In an adaptive blade as described here, the form-fit connection is produced in particular by a first mechanism at the first flexible bar and a second mechanism at the second flexible bar, wherein a convex region at the first mechanism at the first flexible bar engages in a concave region at the second mechanism at the second flexible bar and is displaceable within the latter in the first predetermined direction.

Alternatively or in addition, a convex region at the second mechanism at the second flexible bar can engage in a concave region at the first mechanism at the first flexible bar and can be displaceable therein in the first predetermined direction.

A convex region comprises in particular a lug or a web. A corresponding concave region comprises in particular a groove or a slit in which the lug or the web engages. In particular, the first mechanism at the first flexible bar comprises a T-shaped or L-shaped region which protrudes toward the second flexible bar, and the second mechanism at the second flexible bar comprises one or more T-shaped or L-shaped regions which protrude toward the first flexible bar, wherein beam-shaped portions of the T-shaped or L-shaped regions, or portions with beam-shaped cross sections, which are parallel or substantially parallel to the flexible bars, engage behind one another.

The form-fit connection of the two flexible bars at a location situated proximally with respect to the distal end of the adaptive blade can facilitate a connection of the flexible bars with a constant spacing which does not cause any elastic restoring forces, in contrast to a strut which is itself designed as a flexure bearing or whose ends are designed as flexure bearings.

An adaptive blade as described here further comprises in particular a channel into which at least one of an endoscope, a light source and another medical instrument can be inserted.

The channel can be partially or completely connected to the first flexible bar or to the second flexible bar. In particular, the channel can be partially or completely formed in one piece with the first flexible bar or with the second flexible bar. The channel can have a closed cross section partially, substantially or completely. The channel can have an open cross section partially, substantially or completely, in particular a cross section not fully closed on one side. This can in particular simplify production if the channel and at least one of the two flexible bars are produced as a common molding.

The channel can be composed of a plurality or a multiplicity of segments, which can each be annular or tubular and/or can each have a U-shaped cross section, which segments can be separated by narrow gaps or spacings. Stiffening of a flexible bar to which the channel is connected can in this way be avoided by the channel.

An adaptive blade as described here can be provided and designed for repeated use and repeated sterilization (in particular steam sterilization in an autoclave) or can be provided and designed to be used just once and then disposed of.

An adaptive laryngoscope comprises an adaptive blade, as described here, and a handle, which is mechanically connectable or connected to the proximal end of the adaptive blade.

The adaptive laryngoscope is in particular an intubation laryngoscope and/or is provided for use in microsurgery of the larynx or for other applications in otorhinolaryngology.

The adaptive blade can be formed partially or completely in one piece with the handle, for example as a simultaneously produced molding.

An adaptive laryngoscope as described here further comprises in particular a mechanism for manually moving the proximal end of the second flexible bar relative to the proximal end of the first flexible bar.

The proximal end of the second flexible bar and/or the proximal end of the first flexible bar can be movable relative to the handle by means of the mechanism. For example, the mechanism for manual movement comprises a lever. The lever can be pivotable about a pivot axis that is orthogonal to the adaptive blade and orthogonal to the handle. Alternatively, the mechanism for manual movement can have a push button or a slide, for example a slide that is displaceable parallel to the handle.

An adaptive laryngoscope as described here further comprises in particular a mechanism for alternately locking the proximal end of one of the two flexible bars in one of several positions relative to the proximal end of the other of the two flexible bars.

The mechanism can be designed for alternate locking in one of several predetermined positions (for example by latching or another type of form-fit engagement) or for locking in any desired positions (for example by clamping).

An adaptive laryngoscope as described here further comprises in particular a scale at the handle, at the mechanism for manually moving the proximal end of the second flexible bar relative to the proximal end of the first flexible bar, at the mechanism for alternate locking, at the adaptive blade or at another location, which scale makes it easier to identify or assign or reproduce various relative positions of the proximal ends of the flexible bars.

In a method for adapting a laryngoscope to a patient, proximal ends of flexible bars of a blade of the laryngoscope are displaced relative to each other.

The method is applicable in particular to adaptive laryngoscopes as are described here, and to laryngoscopes with adaptive blades as are described here. The displacement of the proximal ends of the flexible bars of the blade of the laryngoscope is effected in particular manually by means of a lever, a slide or a push button.

In a method for adapting a laryngoscope as described here, the proximal ends of the flexible bars are in particular locked in one of several predetermined relative positions or in any desired relative position.

BRIEF DESCRIPTION OF THE DRAWINGS

Embodiments are explained in more detail below with reference to the attached figures, in which.

DETAILED DESCRIPTION

Figure 1:
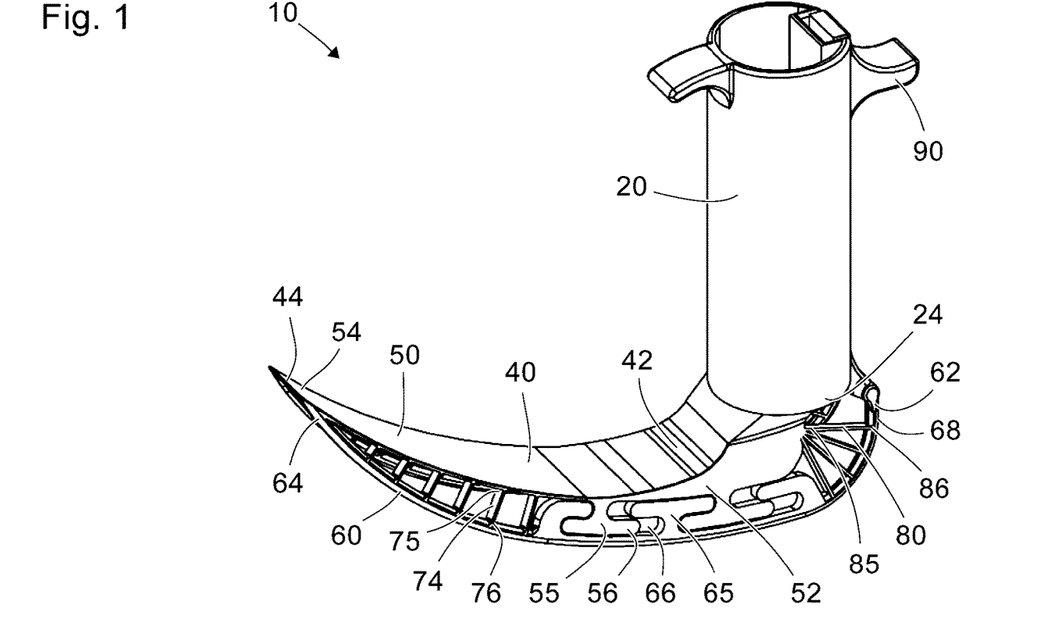
FIG. 1 shows a schematic axonometric view of an adaptive laryngoscope.

FIG. 1 shows a schematic axonometric view of an adaptive laryngoscope, to be more specific of an adaptive intubation laryngoscope 10 with a handle 20 for manually holding and guiding the intubation laryngoscope 10. The adaptive intubation laryngoscope 10 further comprises an adaptive blade 40 with a proximal end 42 and a distal end 44. The adaptive blade 40 is slightly curved and has a cross section that grows smaller toward the distal end 44. The proximal end 42 of the adaptive blade 40 is mechanically connected to the handle 20 in such a way that the region of the adaptive blade 40 adjoining the proximal end encloses an angle of approximately 90 degrees (in the range between approximately 80 degrees and approximately 120 degrees) with the handle 20.

In the example shown, the handle 20 and the adaptive blade 40 are designed substantially in one piece, in particular being largely composed of a single plastic molding. Alternatively, and in contrast to the view in FIG. 1, a coupling mechanism can be provided in the transition region or connecting region 24 between the handle 20 and the adaptive blade 40, in order for the handle 20 and the adaptive blade 40 to be mechanically coupled in such a way that they can be released once or repeatedly and without being destroyed.

The adaptive blade 40 has a first flexible bar 50 and two second flexible bars 60. In the view in FIG. 1, only one of the two second flexible bars 60 is fully visible, the other being concealed behind the first flexible bar 50.

The first flexible bar 50 basically has a broad, flat rectangular cross section. The first flexible bar 50 has a smooth or substantially smooth surface, visible in FIG. 1, for resting on a patient's tongue. The second flexible bars 60 each have basically a square cross section. The distance between the second flexible bars 60 corresponds substantially to the width of the first flexible bar 50.

Near the proximal end 42 of the adaptive blade 40, the second flexible bars 60 are substantially parallel to the edges of the first flexible bar 50. Toward the distal end 44 of the adaptive blade 40, the distances of the second flexible bars 60 from the edges of the first flexible bar 50 decrease. The width of the first flexible bar 50, hence also the distance of the two second flexible bars from each other, also decreases slightly toward the distal end 44 of the adaptive blade 40. At the distal end 44 of the adaptive blade 40, the first flexible bar 50 and the second flexible bars 60 are mechanically connected to each other rigidly.

In a region extending approximately from the proximal end 42 as far as the center of the adaptive blade 40, T-shaped mechanisms 55 are provided at the edges of the first flexible bar 50, and L-shaped or T-shaped mechanisms 65 are provided at the second flexible bars 60. The T-shaped mechanisms 55 at the first flexible bar 50 are oriented toward the second flexible bars 60 and bear on these or are at only a short distance from these. L-shaped or T-shaped mechanisms 65 at the second flexible bars 60 are oriented toward the opposite edges of the first flexible bar 50 and bear on these or are at a slight distance from these.

Slit-like regions 66 are present in each case between a flexible bar 50, 60 and the transverse beam of an L-shaped or T-shaped mechanism 55, 65 connected to the same flexible bar 50, 60. The T-shaped mechanisms 55 at the edges of the first flexible bar 50 and the L-shaped or T-shaped mechanisms 65 at the second flexible bars 60 engage behind each other. For example, a beam-shaped region 56 at the T-shaped mechanism 55 at the first flexible bar 50 is arranged in a slit-like region 66 between one of the two second flexible bars 60, on the one hand, and the T-shaped mechanism 65 thereon, on the other hand. By means of the L-shaped and T-shaped mechanisms 55, 65 engaging mutually one behind the other, the second flexible bars 60 are displaceable in their longitudinal direction relative to the first flexible bar 50, albeit within predetermined limits, but the distances of the second flexible bars 60 from the edges of the first flexible bar 50 are defined by form-fit engagement and can be neither increased nor decreased.

In a distal region, which extends substantially from the center as far as the distal end 44 of the adaptive blade 40, the second flexible bars 60 are connected by struts 74 to the respectively opposite edges of the first flexible bar 50. The struts 74 have cross sections which, in the manner of a flexure bearing, permit a deformation under the forces that occur during the intended use but do not permit any appreciable change of length. In this way, the distances of the second flexible bars 60 from the respectively opposite edges of the first flexible bar 50 are fixed or defined in a substantially unalterable manner, whereas the second flexible bars 60 can be displaced relative to the opposite edges of the first flexible bar 50. The relative movement of the second flexible bars 60 and of the first flexible bar 50 is orthogonal or substantially orthogonal to the struts 74 and therefore, in the configuration indicated in FIG. 1, parallel or substantially parallel to the flexible bars 50, 60.

Arc-shaped portions 68, in particular substantially circular-arc-shaped portions 68, are provided at the proximal ends 62 of the second flexible bars 60. Substantially radially arranged spoke mechanisms 80 are provided between the circular-arc-shaped portions 68 and the handle 20, which transitions at this location into the proximal end 52 of the first flexible bar 50. First, radially inner ends 85 of the spoke mechanisms 80 are mechanically connected to the handle 20 and, by way of the latter, indirectly to the proximal end 52 of the first flexible bar 50. Radially outer second ends 86 of the spoke mechanisms 80 are connected to the arc-shaped portions 68. The entire spoke mechanisms 80, or at least the ends 85, 86 thereof, are flexible or designed as flexure bearings. The cross sections of the spoke mechanisms 80 are chosen such that their length does not change, or does not substantially change, under the forces that occur during the intended use of the intubation laryngoscope 10.

A slide 90 is provided at the handle 20 and can be manually displaced relative to the handle 20 and parallel thereto. One end of the slide 90 is mechanically coupled to the arc-shaped portions 68 or the proximal ends of the second flexible bars 60.

The arc-shaped portions 68 and the spoke mechanisms 80 have the effect that a displacement of the slide 90 parallel to the handle 20 entails a displacement of the second flexible bars 60 relative to the first flexible bar 50. The arc-shaped portions 68 and the spoke mechanisms 80 thus bring about a change of the direction of force and travel through approximately 90 degrees.

Since the flexible bars 50, 60 are mechanically connected to each other rigidly at the distal end 44 of the adaptive blade 40, a displacement of the second flexible bars 60 relative to the first flexible bar 50 causes a change of the curvature of the adaptive blade 40. The curvature of the adaptive blade 40 can thus be altered by displacement of the slide 90 at the handle 20. In order to fix an adopted curvature of the adaptive blade 40, a latch mechanism (not shown in FIG. 1) or other fastening mechanism can be provided.

Figure 2:
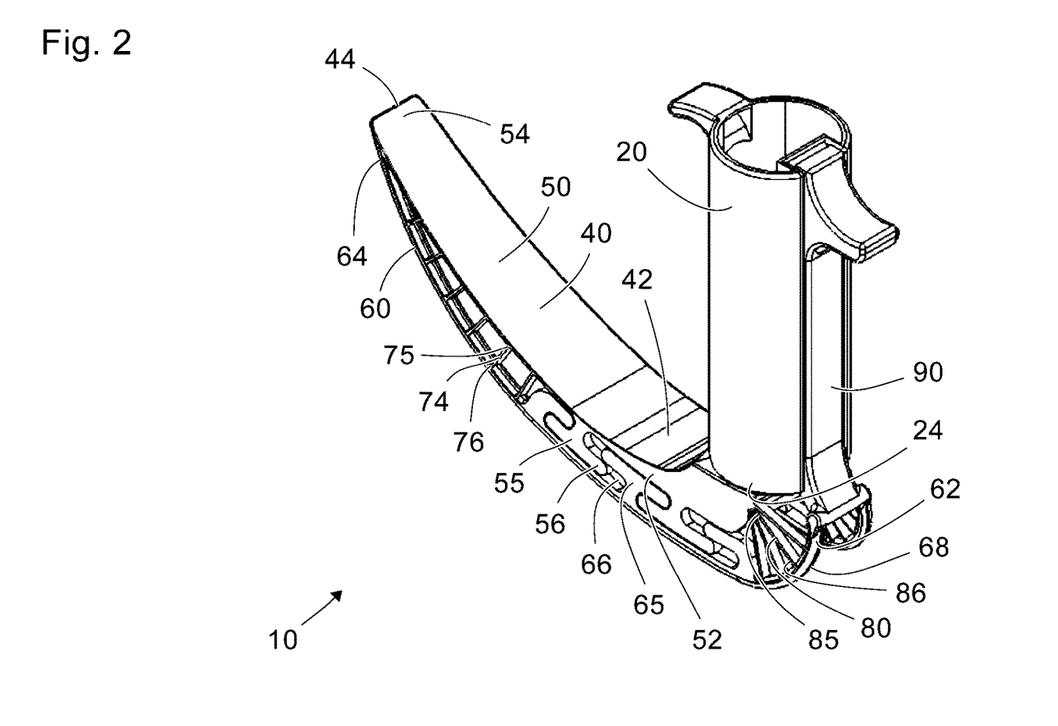
FIG. 2 shows a further schematic axonometric view of the adaptive laryngoscope from FIG. 1.

FIG. 2 shows a further schematic axonometric view of the adaptive intubation laryngoscope 10 shown in FIG. 1. The view in FIG. 2 differs from that of FIG. 1 particularly in terms of the other viewing direction.

It will be seen in FIG. 2 that the slide 90 extends along the entire handle 20. The slide 90 is guided with form-fit engagement in a groove or an open channel. At the end of the handle 20 directed away from the adaptive blade 40, the slide 90 has a lug or a projection that makes it easier to displace manually.

At the end of the handle 20 directed toward the adaptive blade 40, the slide 90 is mechanically connected to the proximal ends 62 of the second flexible bars 60. In particular, the slide 90 is connected to the flexible bars 60 by flexure bearings or other hinges or connected rigidly. The slide 90 and the flexible bars 60 can be formed by a jointly produced molding made of plastic or of another elastic material.

Figure 3:
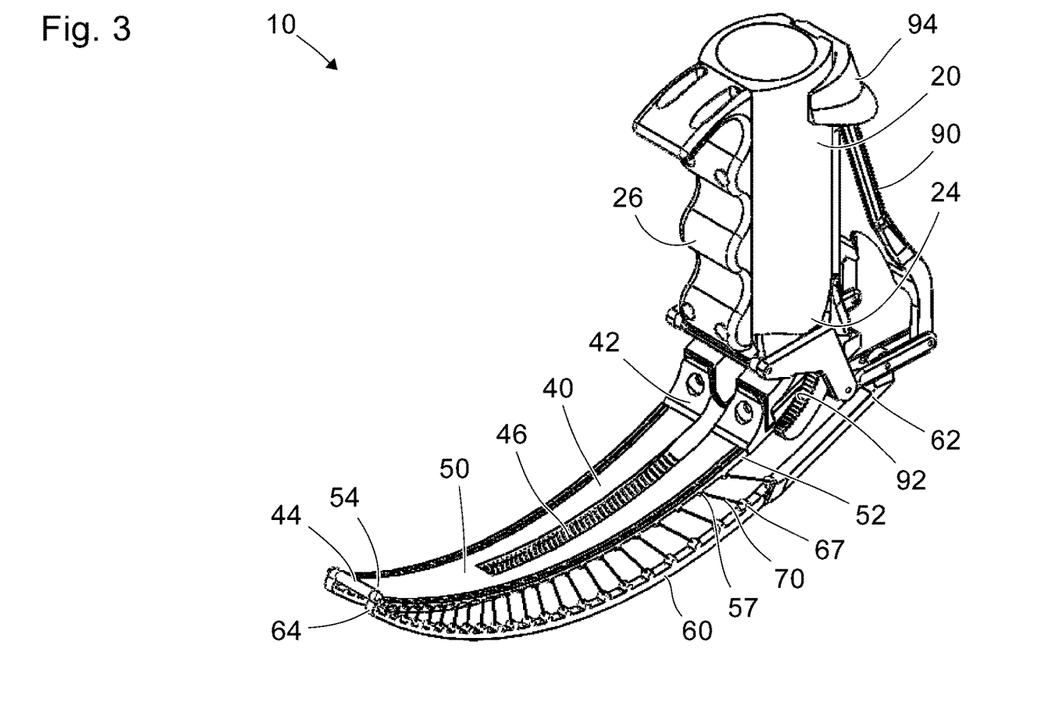
FIG. 3 shows a schematic axonometric view of a further adaptive laryngoscope.

FIG. 3 shows a schematic axonometric view of a further adaptive intubation laryngoscope 10 which, in terms of certain features, properties and functions, is similar to the intubation laryngoscope shown in FIG. 1. Those features, properties and functions of the intubation laryngoscope 10 that distinguish it from the one shown in FIG. 1 are described below.

Eyelets 57, 67 are arranged, respectively, at the edges of the first flexible bar 50 and at the second flexible bars 60. A wire 70, made of a pseudoelastic nickel-titanium alloy, or another thin and flexible component is guided alternately through two adjacent eyelets 57 at the first flexible bar 50 and through two adjacent eyelets 67 at one of the second flexible bars 60, such that the wire has a polygonal meandering configuration. In other words, the wire has a large number of substantially mutually parallel portions which each connect the first flexible bar 50 to one of the second flexible bars 60. The wire 70 transmits tensile forces between the flexible bars 50, 60 and has the effect that the distances between these cannot exceed predetermined maximum values. The wire can be fixed in each of the eyelets 57, 67 or can be displaceable in its longitudinal direction.

A channel 46 for guiding a flexible endoscope or another medical instrument is provided at the first flexible bar 50. The channel 46 is formed by a large number of adjacent arc-shaped or omega-shaped or U-shaped regions at the first flexible bar 50. In this way, the channel 46 does not stiffen the first flexible bar 50.

Alternatively or in addition, a light source, for example a light-emitting diode, or a fiber optic cable for transmission of illumination light can be provided, in which case the light source or the light exit surface is in particular arranged at or near the distal end of the adaptive blade. Alternatively or in addition, a camera or an image sensor with objective or an endoscope can be integrated in the adaptive intubation laryngoscope 10, in which case the camera or the image sensor with objective or the distal end of the endoscope is arranged at or near the distal end of the adaptive blade.

The handle 20 has a pronounced profile 26 at a side where the fingers of a hand holding the handle 20 lie during the intended use. A lever 90 is arranged at an opposite side of the handle 20, where the ball of the thumb lies during the intended use, the free end of the lever 90 being mechanically coupled to the proximal ends 62 of the second flexible bars 60. The lever 90 is coupled to the proximal ends 62 of the second flexible bars 60 in such a way that a pressure exerted on the lever 90 toward the handle 20 causes a displacement of the second flexible bars 60 in the distal direction and an increased curvature of the adaptive blade 40.

A latch mechanism 92 is provided in order to fix an adopted curvature of the adaptive blade 40. The latch mechanism 92 is a mechanism for alternately locking the proximal ends 62 of the second flexible bars 60 in one of several alternative positions relative to the proximal end 52 of the first flexible bar 50. Moreover, a slide 94 is provided at the handle 20, said slide 94 being mechanically coupled to the latch mechanism 92 in such a way that a manual displacement of the slide 94 in a predetermined direction causes unlocking or a release of the adopted curvature.

Figure 4:
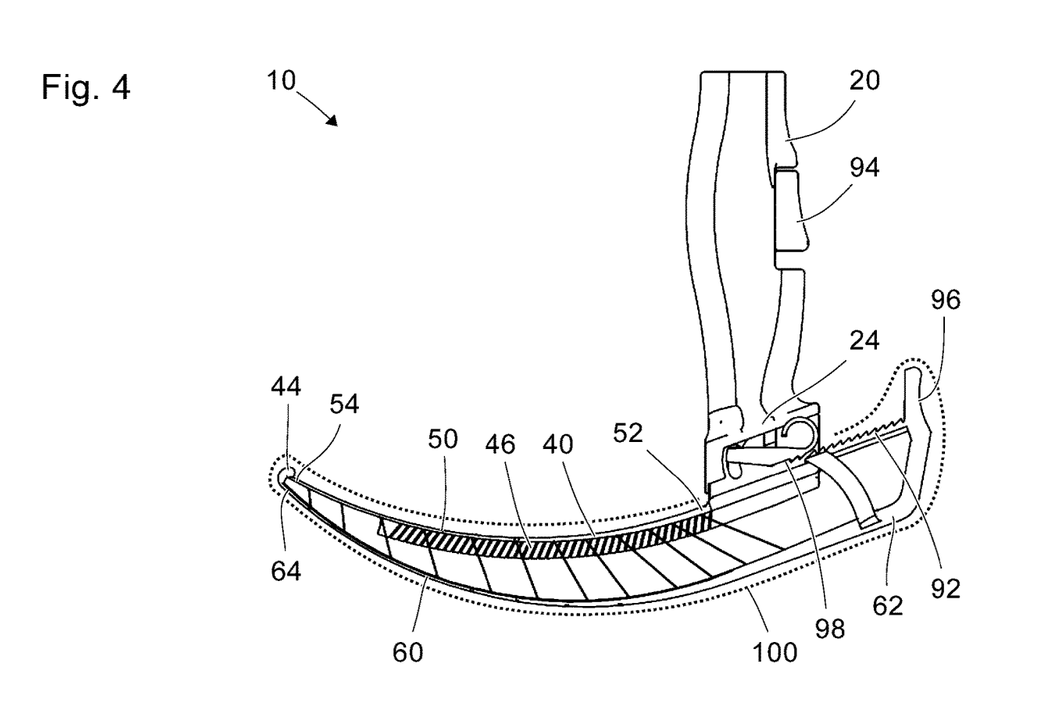
FIG. 4 shows a schematic view of a further adaptive laryngoscope.

FIG. 4 shows a schematic view of a further adaptive intubation laryngoscope 10 which, in terms of certain features, properties and functions, is similar to the intubation laryngoscopes shown in FIGS. 1 to 3, in particular the intubation laryngoscope shown in FIG. 3. Those features, properties and functions of the intubation laryngoscope 10 that distinguish it from the one shown in FIG. 3 are described below in particular.

In the adaptive intubation laryngoscope 10 shown in FIG. 4, the first flexible bar 50 and the second flexible bars 60 are connected to each other by struts 74. The struts 74 can be like the ones described with reference to FIG. 1. Alternatively, the struts 74 can be designed as short wire sections or yarn or filament sections made of metal, plastic or another elastic material, their ends being connected to the flexible bars 50, 60 by form-fit or force-fit engagement or by cohesive bonding. Alternatively, the flexible bars 50, 60 can be formed by a wire, made of a pseudoelastic nickel-titanium alloy, or another thin and flexible component which is alternately fastened to the first flexible bar 50 and to the second flexible bar 60, for example similarly to the example shown in FIG. 3.

In the adaptive intubation laryngoscope 10 shown in FIG. 4, the proximal ends 62 of the second flexible bars 60 are rigidly coupled to a manually displaceable pressure plate 96, particularly designed in one piece with the latter. By moving the pressure plate 96 manually in the distal direction, and therefore toward the handle 20, the second flexible bars 60 can be displaced in the distal direction. On account of the struts 74 between the first flexible bar 50 and the second flexible bars 60, this has the effect of increasing the curvature of the adaptive blade 40.

A latch mechanism 92 is connected rigidly to the pressure plate 96. Movable latching hooks 98 are provided at the connecting region 24 of the handle 20 and of the blade 40. The latch mechanism 92 can hook onto the latching hooks 98 in several alternative predetermined positions, in order to fix several corresponding curvatures of the adaptive blade 40. A slide 94 at the handle 20 is coupled to the movable latching hooks 98 in such a way that a manual displacement of the slide 94 in a predetermined direction causes unlocking or a release of the adopted curvature.

The adaptive blade 40 is optionally surrounded by an elastic jacket 100, the contours of which are indicated by a broken line in FIG. 4. The elastic jacket 100 is formed, for example, from an elastic synthetic film, or from an elastic woven fabric which in particular is provided with a fluid-tight coating. The elastic jacket 100 protects the adaptive blade 40 from contamination and, for example, can be disposed of and replaced after each use. Alternatively, and in contrast to the view in FIG. 4, the jacket 100 can be arranged on the inside.

Figure 5:
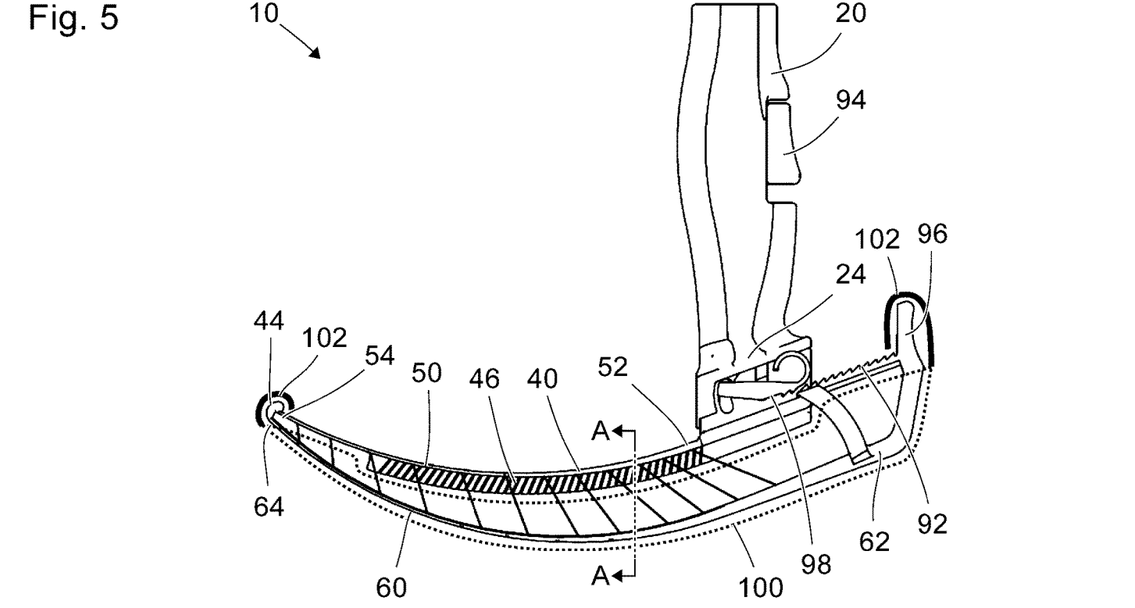
FIG. 5 shows a schematic view of a further adaptive laryngoscope.

FIG. 5 shows a schematic view of a further adaptive intubation laryngoscope 10 which, in terms of certain features, properties and functions, is similar to the intubation laryngoscopes shown in FIGS. 1 to 4, in particular the intubation laryngoscope shown in FIG. 4. Those features, properties and functions of the intubation laryngoscope 10 that distinguish it from the one shown in FIG. 4 are described below in particular.

The adaptive intubation laryngoscope 10 has an elastic jacket 100 similar to the elastic jacket shown in FIG. 4. The elastic jacket 100 has hook-like mechanisms 102 (in particular hook-like ends) which are suspended at the distal end 44 of the adaptive blade 40 and at the pressure plate 96 of the adaptive intubation laryngoscope 10.

Figure 6:
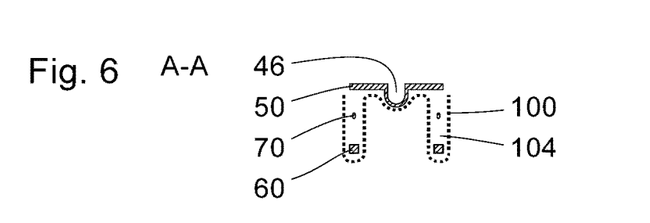
FIG. 6 shows a schematic view of a cross section through the adaptive laryngoscope from FIG. 5.

FIG. 6 shows a schematic view of a cross section through the adaptive intubation laryngoscope 10 from FIG. 5, along the plane A-A which is indicated in FIG. 5 and is orthogonal to the drawing plane of FIG. 5. It will be seen from FIG. 6 that the elastic jacket 100 adopts a trough-shaped or U-shaped configuration between the two second flexible bars 60 and reaches as far as the first flexible bar 50. The elastic jacket 100 forms two pockets or grooves 104, in which the second flexible bars 60 are arranged.

The elastic jacket 100 is clamped at its end between the hook-like mechanisms 102 such that the elastic jacket, on account of the curvature of the adaptive blade 40, is reliably held in the configuration indicated in FIGS. 5 and 6. This can be achieved through different degrees of elasticity of the elastic jacket in the region of its edges, in the regions of the second flexible bars 60, and in its central region adjacent to the first flexible bar 50.

Figure 7:
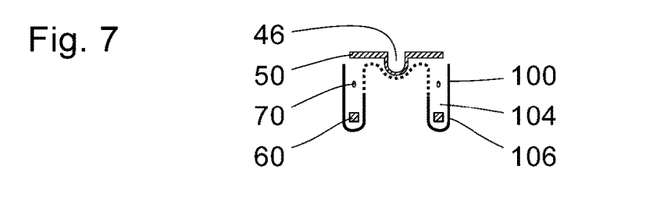
FIG. 7 shows a schematic view of a cross section through a further adaptive laryngoscope.

FIG. 7 shows a schematic view of a cross section through a further adaptive intubation laryngoscope 10 which, in terms of certain features, properties and functions, is similar to the adaptive intubation laryngoscopes shown in FIGS. 1 to 6. Those features, properties and functions of the intubation laryngoscope 10 that distinguish it from the ones shown in FIGS. 4 to 6 are described below in particular.

The adaptive intubation laryngoscope 10 has an elastic jacket 100 similar to the elastic jackets shown in FIGS. 4 to 6. The elastic jacket comprises two stiffened edge regions 106 which form the pockets or grooves 104 for the second flexible bars 60. The stiffened edge regions 106 are in particular stiffened in such a way that their U-shaped cross sections forming the pockets or grooves 104 are reliably maintained even under the great forces that may occur during the intended use of the adaptive intubation laryngoscope.

Figure 8:
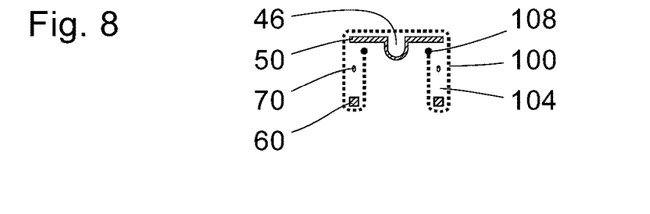
FIG. 8 shows a schematic view of a cross section through a further adaptive laryngoscope.

FIG. 8 shows a schematic view of a cross section through a further adaptive intubation laryngoscope 10 which, in terms of certain features, properties and functions, is similar to the adaptive intubation laryngoscopes shown in FIGS. 1 to 7. Those features, properties and functions of the intubation laryngoscope 10 that distinguish it from the ones shown in FIGS. 4 to 7 are described below in particular.

The adaptive intubation laryngoscope 10 has an elastic jacket 100 similar to the elastic jackets shown in FIGS. 4 to 7. The elastic jacket comprises two pulling mechanisms 108, for example wires, braids or yarns made of rubber or of another material with tensile elasticity. The pulling mechanisms 108 connect the hook-like mechanisms 102 of the elastic jacket 100. The pulling mechanisms 108 can have a tensile elasticity that is less than that of adjacent regions. The pulling mechanisms 108 hold the edges of the elastic jacket 100 near the first flexible bar 50 and therefore between the second flexible bars 60. In this way, the pulling mechanisms 108 make it impossible or difficult for the elastic jacket 100 to slip sideways from the adaptive blade 40.

Certain features and properties of the adaptive intubation laryngoscope shown in FIG. 3 can be combined with features and properties of the adaptive intubation laryngoscope shown in FIGS. 1 and 2. Certain features and properties of the adaptive intubation laryngoscopes shown in FIGS. 4 to 6 can be combined with features and properties of the adaptive intubation laryngoscopes shown in FIGS. 1 to 3. The intubation laryngoscopes shown in FIGS. 1 to 3 can be provided with elastic jackets having the features, properties and functions shown in FIGS. 4 to 8.

In all of the adaptive intubation laryngoscopes shown in FIGS. 1 to 4, it is possible to provide only one second flexible bar instead of two second flexible bars 60. This one second flexible bar 60 can be plate-shaped or designed with a substantially broad and thin cross section, similarly to what has been described for the first flexible bar 50. Alternatively, in all of the adaptive intubation laryngoscopes shown in FIGS. 1 to 4, it is possible to provide three or more second flexible bars.

REFERENCE SIGNS 10 intubation laryngoscope
20 handle of the intubation laryngoscope 10
24 connecting region of the handle 20 and of the blade 40
26 profile at the handle 20
40 adaptive blade of the intubation laryngoscope 10 or for the intubation laryngoscope 10
42 proximal end of the adaptive blade 40
44 distal end of the adaptive blade 40
46 channel for a medical instrument at the adaptive blade 40
50 first flexible bar of the adaptive blade 40
52 proximal end of the first flexible bar 50
54 distal end of the first flexible bar 50
55 T-shaped mechanism at the first flexible bar 50 for form-fit connection to the second flexible bar 60
56 convex region, in particular beam-shaped region, at the T-shaped portion 55 at the first flexible bar 50
57 eyelet at the first flexible bar 50
60 second flexible bar of the adaptive blade 40
62 proximal end of the second flexible bar 60
64 distal end of the second flexible bar 60
65 T-shaped mechanism at the second flexible bar 60 for form-fit connection to the first flexible bar 50
66 concave region, in particular slit-like region, behind the T-shaped mechanism 65 at the second flexible bar 60
67 eyelet at the second flexible bar 60
68 arc-shaped portion at the proximal end of the second flexible bar 60
70 wire or other thin and flexible component
74 strut between the flexible bars 50, 60
75 first end of strut 74, connected to the first flexible bar 50
76 second end of strut 74, connected to the second flexible bar 60
80 spoke mechanism for directly or indirectly connecting the arc-shaped portion 68 at the proximal end 62 of the second flexible bar 60 to the proximal end 52 of the first flexible bar 50
85 first end of the spoke mechanism 80, mechanically connected directly or indirectly to the proximal end 52 of the first flexible bar 50
86 second end of the spoke mechanism 80, mechanically connected directly or indirectly to the arc-shaped portion 68 at the proximal end 62 of the second flexible bar 60
90 slide or lever for manually moving the proximal end 62 of the second flexible bar 60 relative to the proximal end 52 of the first flexible bar 50
92 latch mechanism for alternately locking the proximal end 62 of the second flexible bar 60 in one of several positions relative to the proximal end 52 of the first flexible bar 50
94 slide for unlocking
96 pressure plate
98 movable latching hooks
100 elastic jacket for protecting the adaptive blade 40 from contamination and other environmental influences
102 hook-like mechanism of the elastic jacket 100
104 pocket or groove at the edge of the elastic jacket 100
106 stiffened edge region of the elastic jacket 100
108 pulling mechanism at the edge of the elastic jacket 100

The invention claimed is:

1. An adaptive blade for a laryngoscope, comprising:
   a proximal end, which is mechanically connectable or connected to a handle in order to form an adaptive laryngoscope;
   a first flexible bar, which extends from the proximal end of the adaptive blade to a distal end thereof;
   a second flexible bar, which extends from the proximal end of the adaptive blade to the distal end thereof; and
   a thin and flexible connecting component which is alternately connected to the first flexible bar and to the second flexible bar;
   wherein, at the distal end of the adaptive blade, the flexible bars are connected to each other mechanically rigidly or in an articulated manner;
   wherein, in a proximal direction from the distal end of the adaptive blade, the flexible bars are mechanically connected to each other in such a way that the flexible bars are movable relative to each other substantially in longitudinal directions of the flexible bars;
   wherein the thin and flexible connecting component comprises a wire made of a pseudo-elastic nickel-titanium alloy or of another pseudoelastic material, or a wire made of another material.

2. The adaptive blade according to claim 1, wherein the thin and flexible connecting component is alternatively connected to the first flexible bar and to the second flexible bar in such a way that the thin and flexible connecting component has a meandering configuration.

3. The adaptive blade according to claim 1, further comprising:
   eyelets or other guiding mechanisms at the flexible bars,
   wherein the thin and flexible connecting component is alternately guided through a first group of said eyelets or other guiding mechanisms at the first flexible bar and through a second group of said eyelets or other guiding mechanisms at the second flexible bar.

4. The adaptive blade according to claim 3, wherein the thin and flexible connecting component is mounted displaceably, in each case in a longitudinal direction of the thin and flexible connecting component, in said eyelets or other guiding mechanisms.

5. The adaptive blade according to claim 1, wherein:
   the adaptive blade comprises a plurality of flexible second bars,
   the plurality of flexible second bars are arranged parallel or substantially parallel to each other, and
   the plurality of flexible second bars are spaced apart from each other.

6. The adaptive blade according to claim 1, further comprising:
   a channel into which at least one of an endoscope, a light source, or another medical instrument is configured to be inserted.

7. An adaptive laryngoscope comprising:
   an adaptive blade according to claim 1; and
   a handle, which is mechanically connectable or connected to the proximal end of the adaptive blade.

8. The adaptive laryngoscope according to claim 7, further comprising:
   a mechanism for alternately locking a proximal end of one of the first and second flexible bars in one of several positions relative to a proximal end of the other of the first and second flexible bars.

9. An adaptive blade for a laryngoscope, comprising:
a proximal end, which is mechanically connectable or connected to a handle in order to form an adaptive laryngoscope;
a first flexible bar, which extends from the proximal end of the adaptive blade to a distal end thereof;
a second flexible bar, which extends from the proximal end of the adaptive blade to the distal end thereof; and
a strut which, in a proximal direction from the distal end of the adaptive blade, mechanically connects the first flexible bar and the second flexible bar to each other;
wherein at least one of the entire strut is made elastic or the ends of the strut are connected to the flexible bars by flexure bearings or by other hinges;
wherein, at the distal end of the adaptive blade, the flexible bars are connected to each other mechanically rigidly or in an articulated manner;
wherein, in the proximal direction from the distal end of the adaptive blade, the flexible bars are mechanically connected to each other in such a way that the flexible bars are movable relative to each other substantially in longitudinal directions of the flexible bars.

10. The adaptive blade according to claim 9, wherein:
the adaptive blade comprises a plurality of flexible second bars,
the plurality of flexible second bars are arranged parallel or substantially parallel to each other, and
the plurality of flexible second bars are spaced apart from each other.

11. The adaptive blade according to claim 9, further comprising:
a channel into which at least one of an endoscope, a light source, or another medical instrument is configured to be inserted.

12. An adaptive laryngoscope comprising:
an adaptive blade according to claim 9; and
a handle, which is mechanically connectable or connected to the proximal end of the adaptive blade.

13. The adaptive laryngoscope according to claim 12, further comprising:
a mechanism for alternately locking a proximal end of one of the first and second flexible bars in one of several positions relative to a proximal end of the other of the first and second flexible bars.

14. An adaptive blade for a laryngoscope, comprising:
a proximal end, which is mechanically connectable or connected to a handle in order to form an adaptive laryngoscope;
a first flexible bar, which extends from the proximal end of the adaptive blade to a distal end thereof;
a second flexible bar, which extends from the proximal end of the adaptive blade to the distal end thereof;
an arc-shaped portion at a proximal end of the second flexible bar; and
spoke mechanisms, of which first ends are mechanically connected to a proximal end of the first flexible bar, and of which second ends are mechanically connected to the arc-shaped portion of the second flexible bar;
wherein, at the distal end of the adaptive blade, the flexible bars are connected to each other mechanically rigidly or in an articulated manner;
wherein, in a proximal direction from the distal end of the adaptive blade, the flexible bars are mechanically connected to each other in such a way that the flexible bars are movable relative to each other substantially in longitudinal directions of the flexible bars.

15. The adaptive blade according to claim 14, further comprising:
a form-fit connection of the first and second flexible bars proximally with respect to the distal end of the adaptive blade, wherein the form-fit connection facilitates a movement of the first and second flexible bars relative to each other in a first predetermined direction and, by form-fit engagement, suppresses a movement of the first and second flexible bars relative to each other in a second predetermined direction, which is orthogonal to the first predetermined direction.

16. The adaptive blade according to claim 15, wherein:
the form-fit connection is produced by a first mechanism at the first flexible bar and a second mechanism at the second flexible bar, and
a convex region at the first mechanism at the first flexible bar engages in a concave region at the second mechanism at the second flexible bar and is displaceable within the concave region in the first predetermined direction.

17. The adaptive blade according to claim 14, wherein:
the adaptive blade comprises a plurality of flexible second bars,
the plurality of flexible second bars are arranged parallel or substantially parallel to each other, and
the plurality of flexible second bars are spaced apart from each other.

18. The adaptive blade according to claim 14, further comprising:
a channel into which at least one of an endoscope, a light source, or another medical instrument is configured to be inserted.

19. An adaptive laryngoscope comprising:
an adaptive blade according to claim 14; and
a handle, which is mechanically connectable or connected to the proximal end of the adaptive blade.

* * * * *